US00PP31349P2

(12) United States Plant Patent
van Zoest

(10) Patent No.: US PP31,349 P2
(45) Date of Patent: Jan. 14, 2020

(54) ***CLEMATIS* PLANT NAMED 'ZO12220'**

(50) Latin Name: ***Clematis* hybrid**
Varietal Denomination: Zo12220

(71) Applicant: Jan van Zoest, Boskoop (NL)

(72) Inventor: Jan van Zoest, Boskoop (NL)

(73) Assignee: J. VAN ZOEST BEHEER B.V., Boskoop (NL)

( * ) Notice: Subject to any disclaimer, the term of this patent is extended or adjusted under 35 U.S.C. 154(b) by 0 days.

(21) Appl. No.: 15/998,143

(22) Filed: Jul. 9, 2018

(30) Foreign Application Priority Data

Feb. 8, 2018 (QZ) ..... PBR 20180434

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
See application file for complete search history.

*Primary Examiner* — Susan McCormick Ewoldt
(74) *Attorney, Agent, or Firm* — Penny J. Aguirre

(57) ABSTRACT

A new cultivar of hybrid *Clematis*, 'Zo12220', that is characterized by its free flowering habit as a nursery plant, its terminal and axillary flowers on the new shoots and old wood, its flowers in both spring and summer, and its flowers with tepals that are a blend of different shades of pink surrounding dark red stamens.

2 Drawing Sheets

Botanical classification: *Clematis* hybrid.
Variety denomination: 'Zo12220'.

BACKGROUND OF THE INVENTION

The present invention relates to a new and distinct cultivar of *Clematis* of hybrid origin and will be referred to hereafter by its cultivar name 'Zo12220'. *Clematis* 'Zo12220' is a woody vine grown for use as a landscape plant.

*Clematis* 'Zo12220' was derived from an ongoing breeding program by the Inventor at his nursery in Boskoop, The Netherlands. The goal of the selection was to select a new cultivar of *Clematis* that as a nursery plant was free flowering in spring and summer with terminal and axillary flowers on new shoots using a cane size suitable for nursery production. 'Zo12220' was selected in 2012 and arose from a controlled cross made in 2007 between unnamed and unpatented plants from his breeding program; the female parent designated as No. 20030161 and the male parent designated as No. 19960354.

Asexual propagation of the new cultivar was first accomplished by softwood stem cuttings under the direction of the Inventor in Boskoop, The Netherlands in 2012. Asexual propagation by softwood stem cutting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish *Clematis* 'Zo12220' as a unique cultivar of *Clematis*.

1. 'Zo12220' exhibits a free flowering habit as a nursery plant.
2. 'Zo12220' exhibits terminal and axillary flowers on the new shoots and old wood.

3. 'Zo12220' exhibits flowers in both spring and summer.
4. 'Zo12220' exhibits flowers with tepals that are a blend of different shades of pink surrounding dark red stamens.

The female parent of 'Zo12220' differs from 'Zo12220' in having semi-double flowers in spring, tepals that are violet in color with a much smaller white base, and stamen connectives that are yellow in color. The male parent of 'Zo12220' differs 'Zo12220' in having flowers with tepals that are purple-violet in color, stamen connectives that are straight, and in lacking axillary flowers in spring. 'Zo12220' can be most closely compared to the *Clematis* cultivars 'Hagley Hybrid' (not patented) and 'Pink Fantasy' (not patented). Both are similar to 'Zo12220' in having pink flowers and in producing axillary flowers on shoots. 'Hagley Hybrid' differs from 'Zo12220' in having tepals that are violet in color at the base and have margins that are crinkled and are similar in color to the rest of the tepal, and in having stamen filaments that are pale purple in color. 'Pink Fantasy' differs from 'Zo12220' in having tepal margins that are crinkled and are a similar in color to the rest of the tepal, and in having stamen filaments that are white in color.

BRIEF DESCRIPTION OF THE DRAWINGS

The accompanying colored photographs illustrate the overall appearance and distinct characteristics of the new *Clematis*. The photographs were taken of a two-year-old plant as grown outdoors in a 2-Liter rose container in Boskoop, The Netherlands.

The photograph in FIG. 1 provides a view of 'Zo12220' in bloom in spring.

Figure 1:
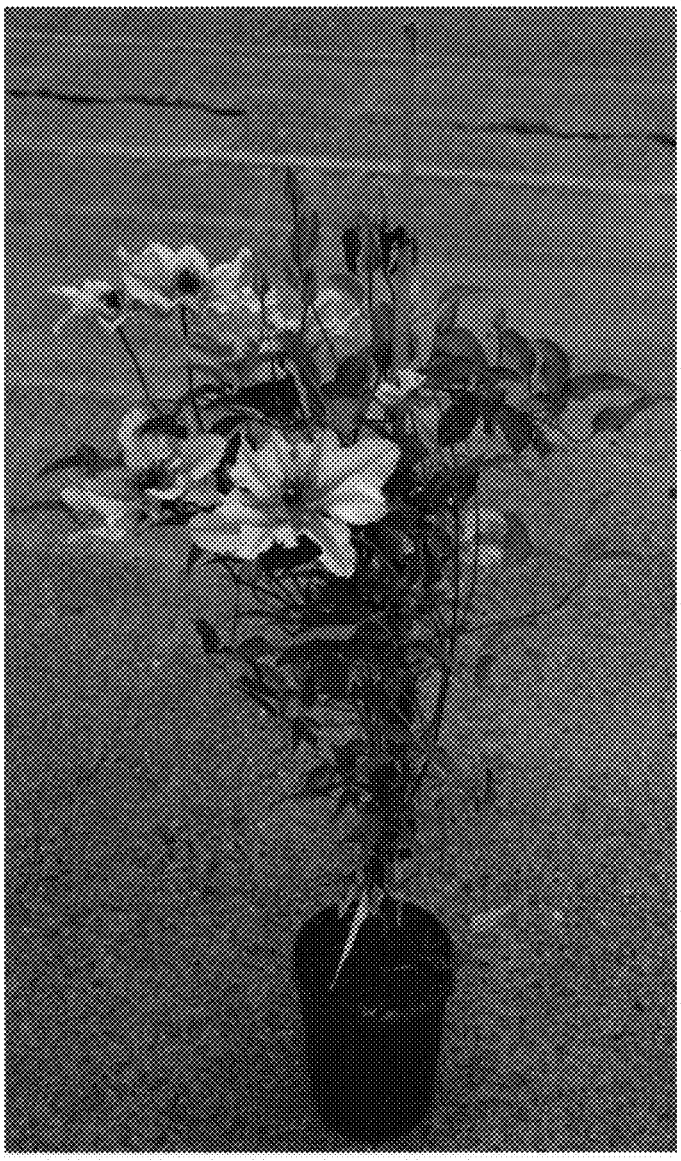
Figure 2:
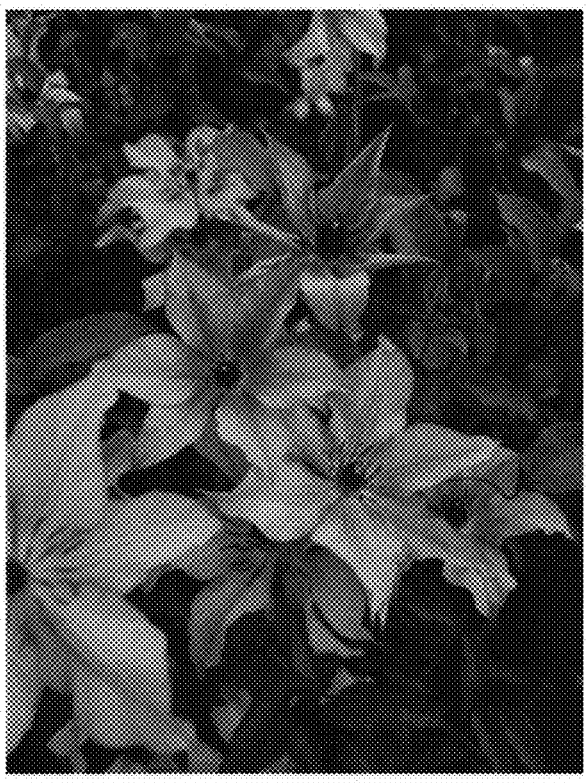

The photograph in FIG. 2 provides a view of the flowers of 'Zo12220' in summer.

Figure 3:
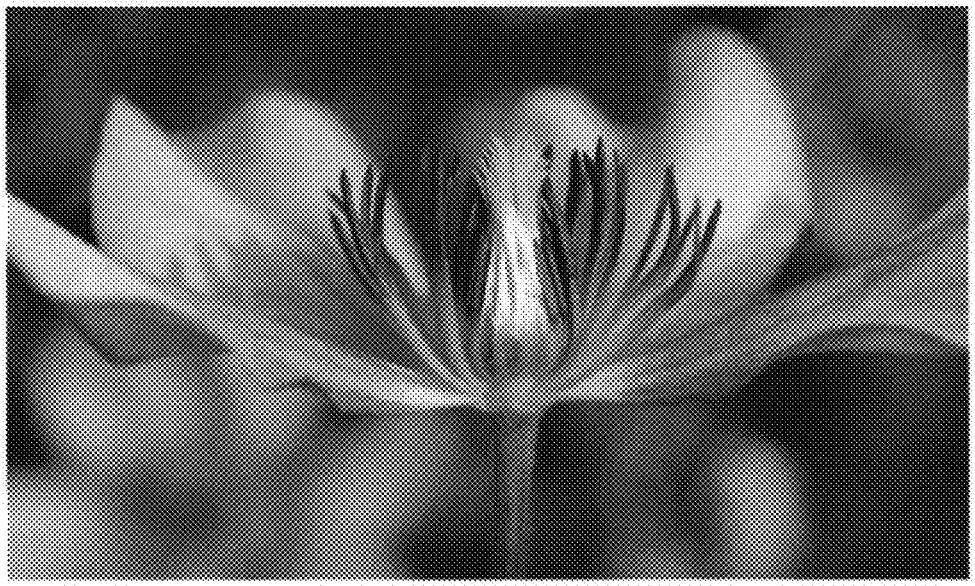

The photograph in FIG. 3 provides a close-up view of a cross section of a flower of 'Zo12220'.

The colors of the photographs are as close as possible with the digital photography techniques available, the color values cited in the detailed botanical description accurately describe the colors of the new *Clematis*.

DETAILED BOTANICAL DESCRIPTION

The following is a detailed description of two-year-old plants as grown outdoors in 2-Liter rose containers in Boskoop, The Netherlands. The phenotype of the new cultivar may vary with variations in environmental, climatic and cultural conditions, as the cultivar has not been tested under all possible environmental conditions. The color determination is in accordance with The 2001 Colour Chart of The Royal Horticultural Society, London, England, except where general color terms of ordinary dictionary significance are used.

General description:

*Botanical classification.*—*Clematis* 'Zo12220'.

*Blooming period.*—Late spring to early Autumn, blooms on old wood and new shoots.

*Plant type.*—Woody vine (stems overwinter).

*Plant habit.*—Climber.

*Height and spread.*—Three-year-old plant reaches an average of 2 m in height and 20 cm in spread at the base.

*Cold hardiness.*—At least to U.S.D.A. Zone 6.

*Culture.*—Moist but well-drained soils in full sun with the roots shaded.

*Diseases and pests.*—Susceptibility to powdery mildew caused by *Erysiphe polygoni* is unknown, no pest problems have been observed.

*Root description.*—Fleshy.

*Propagation.*—Softwood cuttings.

*Root initiation.*—Roots develop in 5 weeks in summer under greenhouse conditions.

*Time required for root development.*—75 to 90 days to fully develop in a 7-cm container from a 5-cm cutting.

*Growth rate.*—Moderately vigorous.

Stem description:

*Shape.*—Round, with 6 ribbed angles.

*Stem color.*—138B, flushed with N77D and becoming 166A with maturity.

*Stem size.*—Up to 2 m in length, an average of 2 mm in width.

*Stem surface.*—Sparsely hairy.

*Internode length.*—Up to 14 cm.

*Branching.*—Primarily from the base.

Foliage description:

*Leaf arrangement.*—Opposite.

*Leaf division.*—Ternate.

*Leaf size.*—Up to 25 cm in length and 18 cm in width.

*Leaf attachment.*—Petiolate.

*Leaf fragrance.*—Slight honey-like fragrance when crushed.

*Leaflet shape.*—Lanceolate.

*Leaflet size.*—Up to 8 cm in length and 3 cm in width.

*Leaflet base.*—Terminal obtuse to cuneate, side leaflets cuneate.

*Leaflet apex.*—Obtuse.

*Leaflet venation.*—Upper and lower surfaces slightly reticulate, 138B in color on both surfaces.

*Leaflet quantity.*—3.

*Leaflet margin.*—Entire and wavy.

*Leaflet surface.*—Upper and lower surface; glabrous, main veins sparsely hairy.

*Leaf color.*—Upper surface; 138A, lower surface; 138B.

*Petioles.*—Up to 9 cm in length, 1.5 mm in diameter, 143C in color, flushed with N77B in color, round in shape, surface sparsely hairy, aspect typically straight and sometimes curling.

*Petiolules.*—Terminal leaflet up to 7 cm in length, articulate towards leaflet, side leaflets up to 3 cm in length, 1 mm in width, round in shape, surface sparsely hairy, 143C in color, flushed with N77B in color, straight to strongly curly.

Inflorescence description:

*Inflorescence type.*—Solitary or a 3-flowered dichasial cyme.

*Inflorescence arrangement.*—Terminal and axillary on old wood in spring and young shoots in summer.

*Peduncles.*—Up to 12 cm in length, 3 mm in width, 138B in color flushed with N77D in color, round in shape, surface sparsely hairy with long hairs.

*Pedicels.*—Up to 9 cm in length, 3 mm in diameter, 138B in color, flushed with N77D in color, round in shape, surface sparsely hairy, densely hairy below the flower.

*Flower buds.*—Upright, lanceolate in shape, up to 5 cm in length and 2 cm in diameter, 143D, flushed with 59D in color, surface densely hairy with long hairs and villous seams.

*Flower fragrance.*—Faint sweet fragrance.

*Lastingness of the flowers.*—Individual flowers last up to 10 days.

*Flower quantity.*—1 to 7 per stem, 40 to 60 flowers on a 3-year-old plant.

*Flower type.*—Rotate, spreading and single.

*Flower aspect.*—Upright.

*Flower shape.*—Round.

*Flower size.*—8 to 12 cm in diameter and 2 cm in depth.

*Flower sex.*—Bisexual.

*Bracts.*—Simple, ovate in shape, up to 5 cm in length and 1 cm in width, acute apex, entire to slightly wavy margin, base is cordate in shape, venation is slightly reticulate, surfaces covered with sparse hairs and glabrous, color; upper surface 138A, veins 138B, lower surface 138B, veins 143C.

*Tepal number.*—Average of 8 in spring, 6 in summer.

*Tepal shape.*—Ovate.

*Tepal aspect.*—Spreading, slightly wavy, overlapping.

*Tepal apex.*—Sub-obtuse.

*Tepal base.*—Cuneate.

*Tepal margin.*—Entire.

*Tepal surface.*—Upper surface; glabrous, lower surface; villous, middle section is villous with long hairs.

*Tepal color.*—Upper surface; N74D with veins N74C, darker towards base 71C, middle 71C, very thin margin 71C, base 145CD, fading to 69C with purple veins 75C and towards the base, middle 75C with 75A veins, base 157D, lower surface; 75C, margin 71C, middle 145C with veins 71C, base 145B, fading to 76C but paler, middle 65C and veins 75B, margin 75A, base 157D.

*Tepal size.*—Up to 8 cm in length and an average of 4 cm in width.

Reproductive organs:

*Gynoecium.*—Average of 150 pistils, up to 1.5 cm in length, ovary; N144C in color and hairy, style;

N155B in color, glossy and plumose, stigma; straight in aspect, 157D in color, glabrous.

*Androecium*.—Filaments; up to 1.4 cm in length, 1 mm in width and linear in shape, surface is glabrous, 71B in color, anthers; 8 mm in length, 1 mm in width, linear in shape, and 59B in color, pollen; 198D in color, moderate in quantity, connective; 1 mm in length, bent in aspect, apex obtuse, surface is glabrous, hairy at the base and 59A in color.

*Seed*.—Present, seed head 4 cm in diameter and globular in shape, seed is up to 75 in quantity, an average of 4 cm in length and 166A in color.

It is claimed:

1. A new and distinct cultivar of *Clematis* plant named 'Zo12220' as herein illustrated and described.

* * * * *